US011969531B2

(12) United States Patent
Marterstock

(10) Patent No.: US 11,969,531 B2
(45) Date of Patent: Apr. 30, 2024

(54) SECURE INPUT ON A CONTROL COMPONENT FOR A DIALYSIS MACHINE

(71) Applicant: Fresenius Medical Care Deutschland GmbH, Bad Homburg (DE)

(72) Inventor: Stefan Konrad Marterstock, Dettelbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1149 days.

(21) Appl. No.: 16/549,124

(22) Filed: Aug. 23, 2019

(65) Prior Publication Data

US 2020/0086029 A1  Mar. 19, 2020

(30) Foreign Application Priority Data

Sep. 19, 2018 (DE) .......................... 102018123012.5

(51) Int. Cl.
*A61M 1/28* (2006.01)
*A61M 1/16* (2006.01)
(Continued)

(52) U.S. Cl.
CPC ............ *A61M 1/28* (2013.01); *A61M 1/1601* (2014.02); *G16H 40/63* (2018.01); *G16H 40/67* (2018.01); *A61M 2205/17* (2013.01); *A61M 2205/276* (2013.01); *A61M 2205/502* (2013.01); *A61M 2205/52* (2013.01); *A61M 2205/80* (2013.01); *A61M 2209/01* (2013.01)

(58) Field of Classification Search
CPC .......... A61M 2209/01; A61M 2205/80; A61M 1/28; A61M 1/1601; A61M 2205/17; A61M 2205/276; A61M 2205/502; A61M 2205/52; A61M 2205/3576; A61M 2205/60; G16H 40/63; G16H 40/67; G16H 20/40

See application file for complete search history.

(56) References Cited

U.S. PATENT DOCUMENTS 5,792,204 A    8/1998  Snell
6,676,621 B1   1/2004  Menninger
(Continued)

FOREIGN PATENT DOCUMENTS

DE  10 2017 111 296 B3  8/2018
WO  WO 2016/156210 A1   10/2016

OTHER PUBLICATIONS

International Patent Application No. PCT/EP2019/074349, Search Report (dated Nov. 28, 2019).
(Continued)

*Primary Examiner* — Robert J Utama
*Assistant Examiner* — Hamza A Darb
(74) *Attorney, Agent, or Firm* — Leydig, Voit & Mayer, Ltd.

(57) ABSTRACT

A medical device, such as a hemodialysis machine or a peritoneal dialysis machine, is provided with control commands in a secure manner based on the commands being detected on a separate control component. The control commands are detected and thereupon a message is generated which contains a request to activate an operating element. Only if the indicated operating element has been activated is the control command forwarded to a dialysis machine for execution.

15 Claims, 6 Drawing Sheets

(51) Int. Cl.
*G16H 20/40* (2018.01)
*G16H 40/63* (2018.01)
*G16H 40/67* (2018.01)

(56) References Cited

U.S. PATENT DOCUMENTS

| | | | |
|---|---|---|---|
| 8,267,921 B2* | 9/2012 | Yodfat | A61M 5/1424 604/93.01 |
| 2005/0022274 A1* | 1/2005 | Campbell | A61M 5/14248 D24/100 |
| 2009/0221890 A1* | 9/2009 | Saffer | A61B 5/742 600/347 |
| 2015/0011970 A1* | 1/2015 | Kamen | G16H 10/65 604/151 |
| 2015/0196258 A1 | 7/2015 | Strickland | |
| 2016/0228633 A1* | 8/2016 | Welsch | G06F 3/015 |

OTHER PUBLICATIONS

German Patent Application No. 10 2018 123 012.5, Office Action (dated Jun. 6, 2019).

* cited by examiner

SECURE INPUT ON A CONTROL COMPONENT FOR A DIALYSIS MACHINE

CROSS-REFERENCE TO RELATED APPLICATION

Priority is claimed to German Patent Application No. DE 102018123012.5, filed on Sep. 19, 2018, the entire disclosure of which is hereby incorporated by reference herein.

FIELD

The invention relates to the secure input of control commands for controlling medical devices, such as dialysis machines, and a protection concept related thereto. The control commands are input on a control component which is provided separately from the device to be controlled.

BACKGROUND

Dialysis machines are blood-treatment apparatuses, in which a fluid of a patient is supplied to a fluid-treatment component via a fluid line, is treated by the fluid-treatment component and is fed back to the patient via the fluid line which can be split into an arterial branch and a venous branch. Examples of such blood-treatment apparatuses include, for example, hemodialysis machines. An example of a blood-treatment apparatus is described in U.S. Pat. No. 6,676,621, the content of which is incorporated by reference herein in its entirety. Hemodialysis, hemofiltration and hemodiafiltration methods are generally performed with automatic hemodialysis machines. A plasmapheresis machine is used to perform plasmapheresis, a blood-treatment method in which the patient's blood is separated into the blood plasma and its corpuscular components (cells). The separated blood plasma is cleaned or replaced by a substitution solution and the cleaned blood plasma or the substitution solution is fed back to the patient. Peritoneal dialysis machines are used to perform peritoneal dialysis in which the abdominal cavity of a patient is filled with a dialysis fluid via a catheter guided through the abdominal wall, the fluid having a concentration gradient of blood substances such as electrolytes (e.g., sodium, calcium and magnesium) compared with the body's own fluids. Toxic substances present in the body pass via the peritoneum acting as a membrane from the blood vessels, extending in the peritoneum, into the abdominal cavity. After several hours, the dialysis fluid located in the patient's abdominal cavity and now with the toxic substances passed from the body added thereto is replaced. Water from the patient's blood can pass via the peritoneum into the dialysis fluid by osmosis, thus dehydrating the patient.

These above-mentioned dialysis machines currently available on the market are generally self-contained, i.e., the program sequence logic for controlling the device is located on the device itself. At least one user interface is formed on the dialysis machine as an input and output unit.

In order to increase flexibility, it is desirable for the dialysis machines also to be controllable on remote control devices.

However, in medical devices, safety requirements are much higher than for other technical apparatuses, and these safety requirements are also to be complied with for remote control in order to be able to reliably prevent on the one hand the misuse of data to be protected (e.g., protected health information (PHI) such as patient-related data) and on the other hand the unintended influence—possibly dangerous to the patient—on the control of the medical device (e.g., by intrusion on the control line).

SUMMARY

In an exemplary embodiment, the invention provides a control component for detecting control commands for securely controlling a medical device. The control component includes: an input interface for detecting at least one control command; an output interface for outputting a message including a request to activate at least one operating element; a processor configured to assign the at least one operating element with an additional function for checking whether the activation thereof has been detected; and the at least one operating element, wherein the at least one operating element is controlled by the processor and checks whether the activation thereof has been detected, and wherein the at least one operating element is configured to send a confirmation signal to the processor in response to the activation thereof being detected. The processor is configured to cause execution of the at least one control command on the medical device only in response to receiving the confirmation signal from the at least one operating element.

In another exemplary embodiment, the invention provides a method for operating a control component for detecting control commands for securely controlling a medical device, wherein the control component is arranged separately from the medical device and communicates with the medical device via a secure communications connection. The method includes: detecting, by the control component, at least one control command; generating, by the control component, a message including a request to activate at least one operating element; outputting, by the control component, the message; checking, by the control component, whether activation of the at least one operating element has been detected on the at least one operating element; and in response to detecting activation of the at least one operating element, preparing the at least one control command for execution on the medical device.

In yet another exemplary embodiment, the invention provides a non-transitory computer-readable medium having processor-executable instructions stored thereon for operating a control component for detecting control commands for securely controlling a medical device, wherein the control component is arranged separately from the medical device and communicates with the medical device via a secure communications connection. The processor-executable instructions, when executed, facilitate: detecting, by the control component, at least one control command; generating, by the control component, a message including a request to activate at least one operating element; outputting, by the control component, the message; checking, by the control component, whether activation of the at least one operating element has been detected on the at least one operating element; and in response to detecting activation of the at least one operating element, preparing the at least one control command for execution on the medical device.

In yet another exemplary embodiment, the invention provides a control system for detecting control commands on a control component which is configured for securely controlling a medical device. The control system includes: the medical device; the control component; and at least one operating element. The control component is arranged separately from the medical device and is configured to communicate with the medical device via a secure communications connection. The control component or the medical device is configured to detect a control command. The control component is configured to generate a message which includes a request to activate the at least one operating element. The control component or the medical device is configured to output the generated message. The at least one operating element is configured to check as to whether an activation of the at least one operating element has been detected. The medical device is configured to execute the at least one control command based on the activation of the at least one operating element having been detected.

BRIEF DESCRIPTION OF THE FIGURES

Exemplary embodiments of the present invention will be described in even greater detail below based on the exemplary figures. The invention is not limited to the exemplary embodiments. All features described and/or illustrated herein can be used alone or combined in different combinations in embodiments of the invention. Features and advantages of various embodiments of the present invention will become apparent by reading the following detailed description with reference to the attached drawings which illustrate the following.

DETAILED DESCRIPTION

Figure 1:
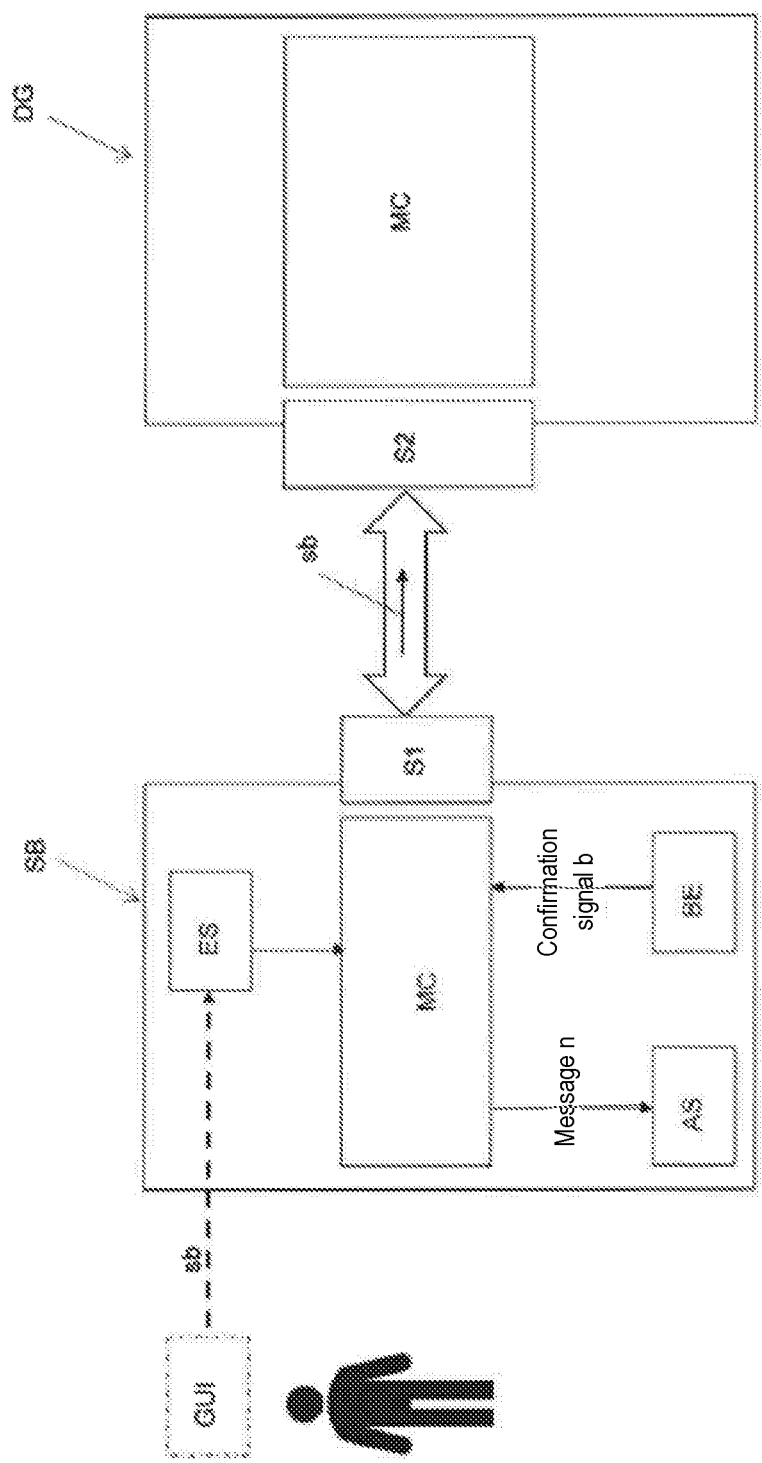
FIG. 1 shows a schematic illustration of a dialysis machine for which control commands are to be securely detected on a separately provided control component, in accordance with an advantageous embodiment of the invention.

Exemplary embodiments of the present invention provide an improved safety concept for a medical device or a group of these devices which permits on the one hand increased flexibility for inputting control commands and on the other hand can also meet the increased safety requirements by way of structural, constructional measures.

An exemplary embodiment of the invention is described hereinafter with respect to a medical device and a control component. Features, advantages or alternative embodiments mentioned herein are likewise also applicable to other exemplary embodiments. For example, methods described herein can also be developed with the features which are described in conjunction with the control component, and vice versa. In so doing, the corresponding functional features of the method are embodied by corresponding physical components, such as by electronic hardware modules or digital processing units (such as microcontroller modules or microprocessor units), of the system or of the product, and vice versa. For instance, a control command can be detected by a corresponding input interface which can be formed as a button on a (graphical) user interface.

According to a first aspect, the invention relates to a control component for securely detecting control commands used to control at least one medical device, such as at least one dialysis machine, having:

an input interface for detecting at least one control command;

an output interface for outputting a message including a request to activate at least one operating element;

a processor configured to implement a safety algorithm in that the processor itself checks, or assigns the at least one operating element with an additional function for checking, whether the activation (e.g., based on detecting an activation signal on the operating element) has been detected on the at least one operating element;

at least one operating element which is controlled by the processor and checks, according to its assignment from the processor, whether the activation has been detected, and wherein the at least one operating element is designated to send a confirmation signal to the processor when the activation is detected;

wherein the processor of the control component only allows the usage (or execution) of the at least one control command on the medical device when it has received the actuation signal from the at least one operating element.

In a preferred embodiment of the invention, provision is made that the control command is detected on the control component. Provision can then, for example, also be made that the control command is only sent to the medical device when the confirmation signal has been received.

In a preferred embodiment of the invention, the input interface and the at least one operating element are components separated from each other from a technical point of view. The aforementioned elements can be implemented as different input channels (e.g., touch keys and/or hard keys) which can be read by a processor (preferably in the control component). This has the advantage that the input can be confirmed once again on another medium (element of the control component). Therefore, the input can be made secure via an additional input channel.

In a further preferred embodiment of the invention, the control component is arranged separately from the medical device or is provided as a separate device. The control component communicates with the medical device via a secure communications connection. Alternatively, the control component can also be formed on the medical device.

In a further preferred embodiment of the invention, the output interface and the input interface are combined in one component. The combined component can be formed, for example, as a user interface—such as a graphical user interface (GUI).

In another preferred embodiment of the invention, the message includes a summary element which reproduces the at least one control command (or the result thereof) detected on the input interface. The summary element preferably reproduces the control commands in another format. For example, if the commands were input acoustically, they could be reproduced in text format or as characters in the summary element. In another example, if the commands were input via a menu selection, they can be reproduced in text format, or vice versa. Therefore, the confirmation security and thus also the quality of the entire process can be improved because errors are frequently recognized in a repeated illustration (such as with a change in format).

According to a further aspect, the invention provides a protective method for operating a control component for securely detecting control commands for controlling at least one medical device (e.g., at least one dialysis machine), wherein the control component is provided separately from the medical device and communicates with the medical device via a secure communications connection, comprising the following method steps:

detecting at least one control command;

generating a message including a request to activate at least one operating element;

outputting the generated message;

checking whether an activation has been detected on the at least one operating element, and if so:

(locally or internally) preparing the detected at least one control command for execution on the medical device.

According to a preferred embodiment of the protective method, the control command is detected as an acoustic input (voice input) and/or as a gesture input (for gesture control) and/or as an input on a user interface. Alternatively, a menu selection can be used as the input. Therefore, the flexibility of the input can be increased.

In a further preferred embodiment of the invention, monitoring is performed as to whether an activation has already been detected on the at least one operating element at a point in time before outputting of the message, and if so: a warning is output. Therefore, the technical advantage is achieved that it can be automatically recognized if, for example, an operating element is no longer functioning without any problems and is so to speak "permanently activated" because, for example, a button is jammed.

In a further preferred embodiment of the invention, the at least one control command is not detected on the operating element (but rather on another structural unit such as on a second channel). Alternatively or cumulatively, the activation is not performed or detected on an input interface on which the at least one control command is detected. Therefore, the safety can be increased in that a separate component activation or operation is necessary, and so the separate component can be used as a reference or independent confirmation and thus as a verification.

In a further preferred embodiment of the invention, the at least one control command and/or the message comprises a time stamp. Therefore, a check between the input and confirmation can be performed in an even more precise manner and also in terms of time.

In a further preferred embodiment of the invention, the request to activate at least one (particular) operating element from a group of operating elements is generated dynamically in accordance with a preconfigured plan (or scheme) stored in a memory. The plan can be stored consistently and constantly for all control commands to be confirmed. Alternatively, the plan can be different for each control command or a group of control commands. For instance, the plan can also differ from control command to control command. The plan can designate, for example, in which form and/or when an operating element is to be activated. For example, it can be configured that initially a first operating element and then a second operating element has to be activated. If an operating element is, for example, a button on a GUI, then a single click or a double-click may be required. These settings of the plan are configured in a preparation phase of the protective method.

In another preferred embodiment of the invention, the request to activate at least one operating element is a request to activate a plurality of operating elements in a defined sequence or a request for simultaneous activation. Therefore, the safety can be increased in that not only one activation process but a plurality of activation processes can be performed in a predefined sequence. Therefore, the sequence must be observed and the operating element must also be operated in the correct manner. This means double security.

In another preferred embodiment of the invention, the protective method is implemented in a protected memory region of the control component.

According to a further aspect, the invention provides a computer program for a medical device and/or a control component which can be loaded into an internal memory of a processor and includes software routines, via which the steps of the foregoing method are performed when the software routines are executed on the processor. The protective method and/or the safety algorithm can thus be executed in a completely automatic, computer-implemented manner and without user interaction.

According to a further aspect, the invention provides a control system for securely detecting control commands on a control component configured to control at least one medical device (e.g., a dialysis machine). The system is formed with:

the at least one medical device;

the control component;

at least one operating element;

wherein the control component is arranged separately from the medical device and communicates with the medical device via a secure communications connection and thus is formed so to speak as a distributed system;

wherein a control command is detected on the control component or on the medical device and a message is generated which includes a request to activate the at least one operating element;

wherein the generated message is output on the control component or on the medical device; and wherein on the at least one operating element or using the at least one operating element a check is made as to whether an activation has been detected and wherein if so (and thus the detected at least one control command is deemed to be confirmed): causing the detected at least one control command to be executed on the medical device.

The protective method can comprise a plurality of stages which are performed on different computer-based entities. For instance, a first stage of the protective method can be performed on the control component and a second stage can be performed on the medical device and/or on a separate entity. It is also possible for all the method steps of the protective system to be performed on the control component. Alternatively, it is possible for some method steps, such as inputting the at least one control command and/or the evaluation, to be effected in full by the medical device.

The control component may be an electronic terminal having a processor or microprocessor which performs a safety algorithm for making an input (e.g., a control command as a user input of a user) for securely controlling the medical device. The control component can be formed directly or indirectly with a user interface. In this context, "indirect(ly)" means that the user interface can also be formed on an external device (e.g., a mobile radio device) which exchanges data with the control component via a corresponding network connection (e.g., a wireless local area network (WLAN)) or interface. The control component also communicates data with the medical device. This is preferably secure. The control component can be formed as a mobile radio device or as a tablet, smartphone or mobile terminal. In a variant, the control component can be formed as a server. The control component can be configured to (centrally) control a plurality of medical devices.

The control component is controlled, for example, by a processor. The software implemented in the processor controls the operating elements of the control component. In accordance with the invention, the safety algorithm modifies this software in order to assign additional functionality to all the operating elements or selected ones thereof. For this purpose, an operating element is determined in accordance with a preconfigurable plan on which a user action must be performed in order to confirm the input control command displayed in a summarized manner. This can be performed, for example, by moving a switch or by clicking a button on a user interface or by pressing or actuating a key, for example, the volume buttons on a tablet or smartphone. As soon as the provided activation of the operating element is detected, the operating element sends a confirmation signal to the processor which thereupon designates the respective control command as being confirmed and causes the execution of the control command on the medical device. This can occasionally occur by sending the control command to the medical device.

A secure communications connection between the control component and the medical device to be controlled is provided. The inputs detected on the control component as control commands are subsequently used to control the medical device and therefore must additionally be secure. This is accomplished in that each input must be confirmed by a different (other) operating element of the control component. The operating element to be actuated is selected in accordance with a predefined plan which is implemented via a safety algorithm. The safety algorithm is implemented in the processor of the control component and can be stored in a (preferably) secure memory region. The secure communications connection can thus be configured preferably for bidirectional data exchange.

The medical device can be an electronic device which provides medical functions. It can be a dialysis machine or another blood-treatment apparatus. The medical device has a processor, for example, a digital circuit which undertakes control tasks.

The control command is used to control the medical device and is executed and implemented locally on the device. It can be, for example, a single command (activate/deactivate pump) or a sequence of commands (e.g., replace extracorporeal blood-treatment module). The control command is provided in a format which can be implemented by the processor of the medical device.

The safety algorithm is fully computer-implemented and is automatically performed without user interactions. The safety algorithm is used to actuate the operating elements of the control component in a modified manner (e.g., the "turn up loudspeaker" button is allocated the other or additional function of detecting whether or not an activation or actuation by the user has taken place. The button or operating element thus becomes a checking element for confirming an already input control command by activating a button or a configurable switching element or component on the control component. The safety algorithm can be implemented in the processor of the control component and/or in the processor of the dialysis machine. Configurations determined in a configuration phase can be made and stored by the user in advance, for instance, the plan for activating the operating elements. A setting can be made as to which operating elements (switches, keys, buttons, knobs, etc.) have to be activated by which actions (single click or repeated clicking, pressing, switching, rotating, etc.) for confirmation. In order to increase the security, a configuration can be provided that not only one confirmation element (e.g., loudspeaker button) has to be activated but rather a series of confirmations elements have to be activated in a configurable sequence.

The confirmation signal is an electronic signal and can be binary (can be 0 or 1 in order to signal successful or incorrect confirmation of the operating element) or can be a sequence of bits (encoded). The confirmation signal is sent by the respective operating element to the processor of the respective device (control component or medical device).

The message is electronic and includes at least one digital data set. The message contains at least one request to activate the at least one operating element. The message is directed to the user and is output on the output unit (e.g., GUI). The message can include, for example, an instruction in text format (e.g., "Please now activate the operating element of device XY to position xyz in the described manner"). For this, a pictorial instruction can be output showing where the operating element is located and/or a simulated illustration of how to activate it. In a preferred embodiment of the invention, the message includes a summary element. This can be, for example, a data field in order to display to the user the control command detected on the input interface once again repeatedly as a text-based summary for confirmation. In addition, a confirmation field can be provided for the user, via which he can confirm or reject the input of his control command. In the case of a rejection, the protective method is interrupted. In the case of a confirmation, the method continues. It is also feasible for the confirmation signal to be able to be transmitted by a voice input from the operator.

Checking (whether the provided operating element has been activated in the provided manner) is preferably effected continuously and/or multiple times as soon as the first input is possible and then in an event-based manner, for example, as soon as an activation is detected or as soon as a message is received. It is thus ensured that the functionality of the respective operating element can be monitored. If a confirmation signal is already detected on the operating element prior to the request for activating the operating element, it can be assumed that an error has occurred (button jammed) and a corresponding warning can be output.

The protective method and/or the safety algorithm can be provided as a computer program, such as a microprocessor program.

In another exemplary embodiment, the invention provides a computer program product which is, or can be, loaded into a memory of a computer or of an electronic or medical device, with a computer program to carry out the method described above when the computer program is executed on the computer or the electronic or medical device.

In another exemplary embodiment, the invention provides a computer program for carrying out the method described above when the computer program is executed on a computer or an electronic or medical device. It is possible for the computer program to be stored on a medium which can be read by the computer or the electronic or medical device.

In the following detailed description of the figures, exemplary embodiments, which are to be understood to be non-limiting, together with the features and further advantages thereof will be discussed with the aid of the drawings.

The invention will be explained in more detail hereinafter with reference to exemplary embodiments in conjunction with the figures. The following description of the exemplary embodiments relates to a dialysis machine DG as an example of a medical device. In a preferred embodiment of the invention, a control component SB and a dialysis machine DG are both formed with a processor MC. In order to keep the description as clear as possible, each of the multiple processors is labeled with MC. It will be clearly apparent from context in the following description which respective processor is being referred to.

FIG. 1 shows a dialysis machine DG as an example of a medical device which is to be controlled by a control component SB. The user performs inputs with control commands sb on the control component SB. For this purpose, the control component SB can be formed with an input interface ES. Alternatively, it is also possible for the input interface ES, as shown as a broken line in FIG. 1, to be formed externally and outside of the control component SB, for example, as a graphical user interface GUI which exchanges data with the control component SB. The control commands sb detected on the input interface are passed to the local processor MC of the control component SB, which causes the generation of a message n which is output on an output interface AS. The message n contains a request to activate an operating element BE and, if need be, can also include further instructions and data fields for notification purposes. The operating element BE indicated in the request is monitored. In particular, a check is made as to whether activation has occurred. If so, a confirmation signal b is transmitted to the processor MC of the control component SB. The processor of the control component SB is now able to decide whether or not the operating element has been operated and activated as provided by the safety algorithm. If so (confirmation signal b received), it can make local preparations in order for the control command sb to be implemented and executed on the dialysis machine DG. For this purpose, it can particularly cause the sending of the control command sb to the dialysis machine DG over a secure data connection. After receipt of the control command sb on the dialysis machine DG, the command can be executed thereon.

In this exemplary embodiment, provision is made that the protective method is performed in full on the control component SB. The user thus remotely controls the dialysis machine from the control component SB.

Figure 2:
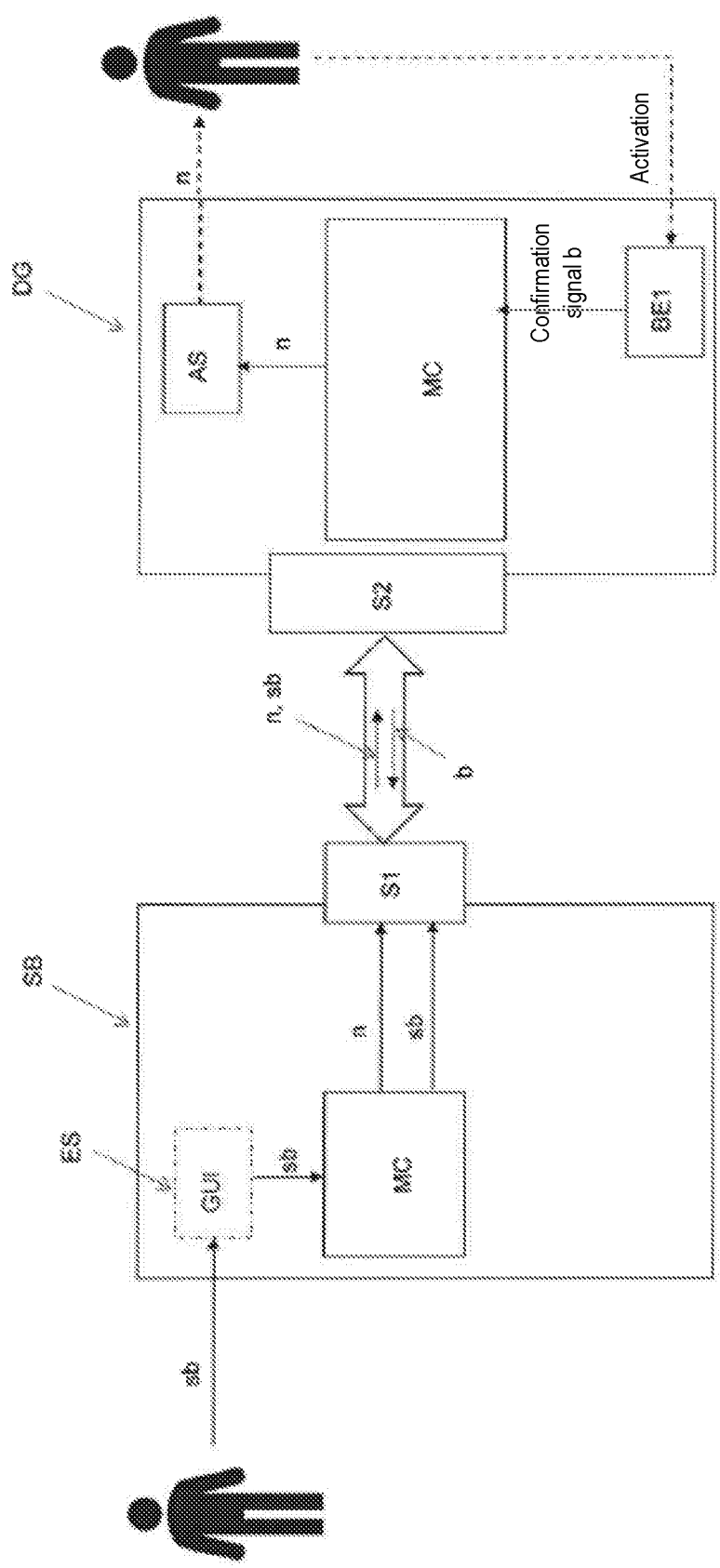
FIG. 2 is an alternative implementation of the exemplary embodiment illustrated in FIG. 1.

An alternative variant is illustrated in FIG. 2. In this case, for example, a four-eyes principle can be used to control the dialysis machine DG. A first user operates the control component SB and a second user operates the dialysis machine DG. A control command sb is detected from the first user on the control component SB, for example on a user interface GUI, and is forwarded to the processor MC of the control component SB which, in response thereto, generates the message n and sends it to the dialysis machine DG via the secure data connection. The local processor MC of the dialysis machine DG forwards the received message n to the local output interface AS for outputting (to the second user). The message n contains the request to activate an operating element BE1, which is arranged on the dialysis machine DG and can be operated by the second user or by the first user. The operating element BE1 is actuated by the processor MC of the control component SB in accordance with the safety algorithm such that, upon correct activation (e.g., by detecting an activation signal), it sends the confirmation signal b to the processor MC of the dialysis machine DG.

In a further variant, the control command sb is input on the control component SB and the message n output likewise on the control component SB, but the input is confirmed on the dialysis machine DG (e.g., via a dedicated confirmation switch). The message n can also be formed as a voice message for outputting on the control component SB (e.g., reproduction of the user input or the control command spoken out loud with a request for confirmation).

In another variant, the confirmation signal b is forwarded (from the dialysis machine DG) to the control component SB which, in response thereto, transmits the (confirmed) control command sb to the processor MC of the dialysis machine DG.

In another variant, not only is the locally generated message n (or in an alternative embodiment of the invention the message also generated on the dialysis machine DG) sent by the control component SB to the dialysis machine DG for confirmation, but additionally also the detected control command sb. In this case, the confirmation signal b does not have to be sent by the dialysis machine DG to the control component SB because the dialysis machine is already aware of the control command sb and can execute it directly. If a confirmation signal has not been detected, the provided, but unconfirmed, control command sb is deleted and not executed.

Figure 3:
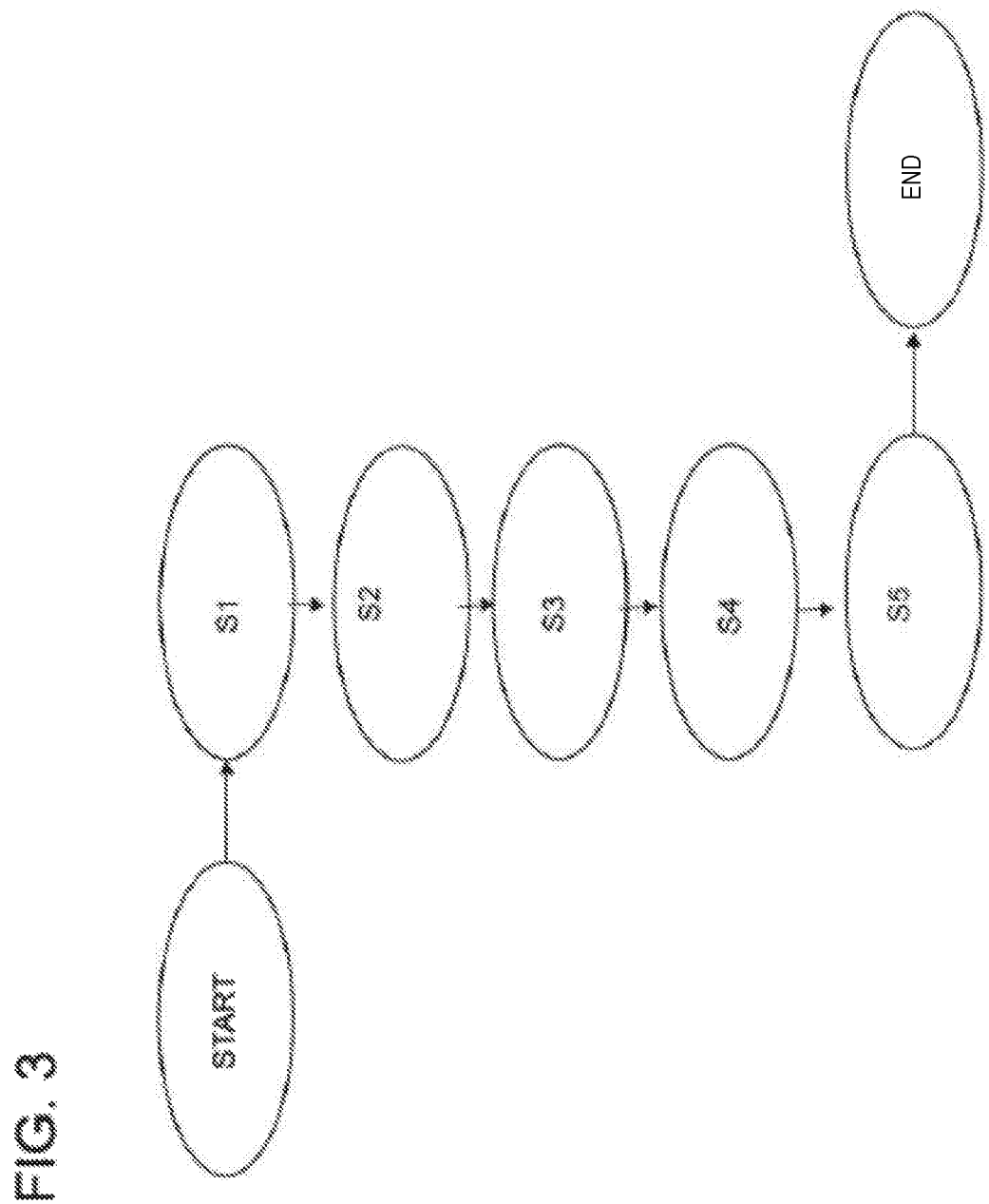
FIG. 3 is an exemplary flow diagram of method steps of a protective method according to an advantageous embodiment of the invention.

FIG. 3 shows a process in an exemplary embodiment corresponding to the system depicted in FIG. 1. After the start of the method, the control command sb is detected in step S1, preferably on the input interface ES. In step S2, the message n is generated. In step S3, the generated message n is output, preferably on the output interface AS. In step S4, a check is made as to whether the operating element BE has been activated as provided (according to the request). For this purpose, a check is made or monitoring is performed as to whether a confirmation signal b has been detected on the operating element BE and transmitted to the processor MC of the control component SB. In step S5, the control command is prepared for local execution on the dialysis machine DG in step S6.

In an alternative configuration, for example as discussed above with respect to the system depicted in FIG. 2, in order to minimize the safety requirements of the control component SB, provision is preferably made that as many steps as possible, in particular the evaluation, are performed on the dialysis machine DG itself. It is thus helpful if an operating element BE1 is formed on the dialysis machine, as explained above in conjunction with FIG. 2. Preferably, the control component SB is therefore configured "only" for data input and output, while the evaluation logic with the check as to whether or not activation of the operating element has occurred is performed on the dialysis machine itself. Therefore, the safety standards can be adhered to more easily.

Figure 4:
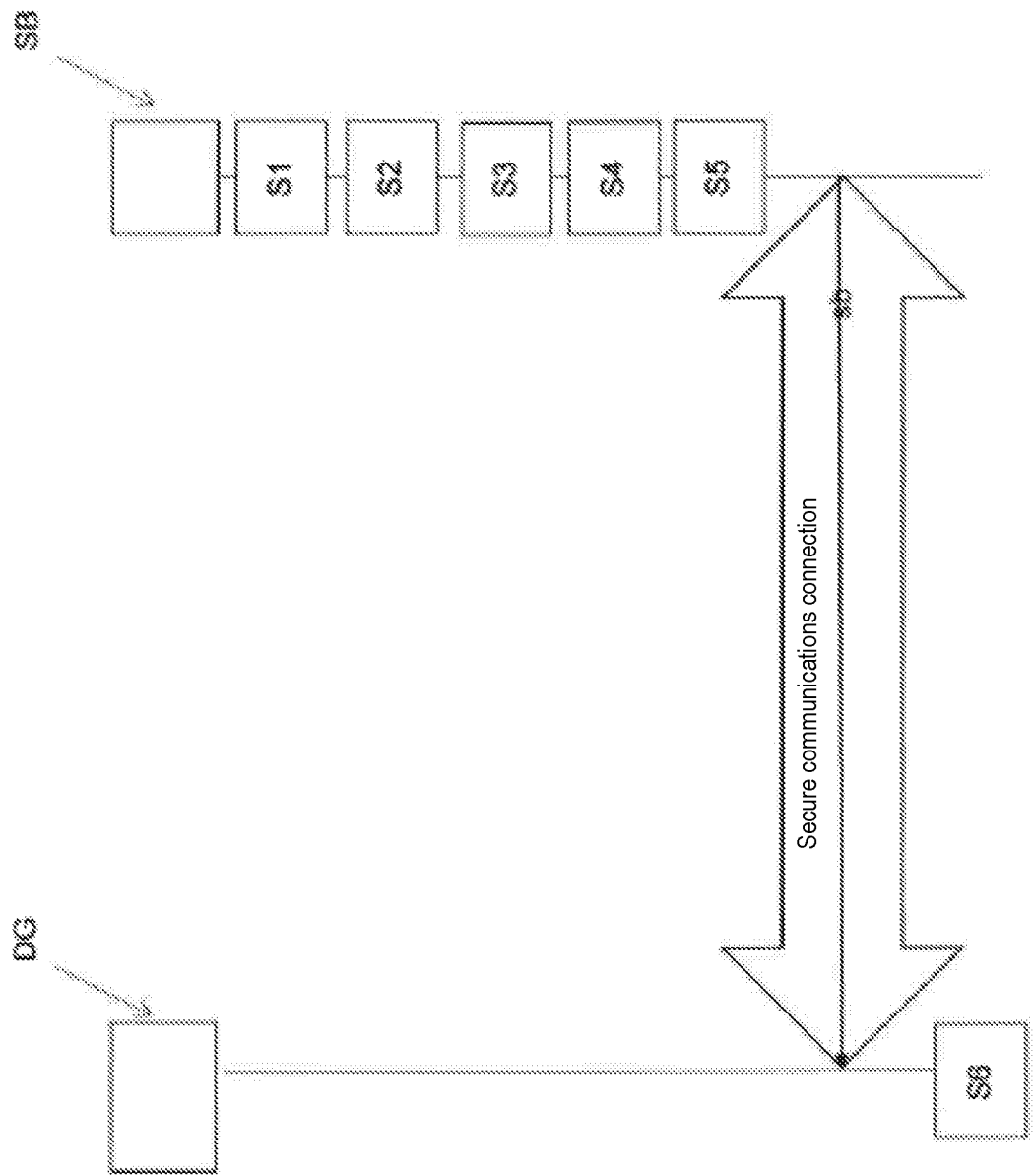
FIG. 4 shows an exemplary interaction diagram with data exchange of signals and messages between the control component and a dialysis machine.

FIG. 4 is an interaction diagram between the dialysis machine DG and the control component SB. In the variant shown in FIG. 4, all the steps of the protective method are performed on the control component SB. Only after a successful confirmation is detected on the control component SB is the control command sb sent to the dialysis machine DG for local execution. Otherwise, the control command is not implemented and must be input repeatedly if need be. The interactions in FIG. 4 correspond to the structural design of the protective system described above with reference to FIG. 1.

Figure 5:
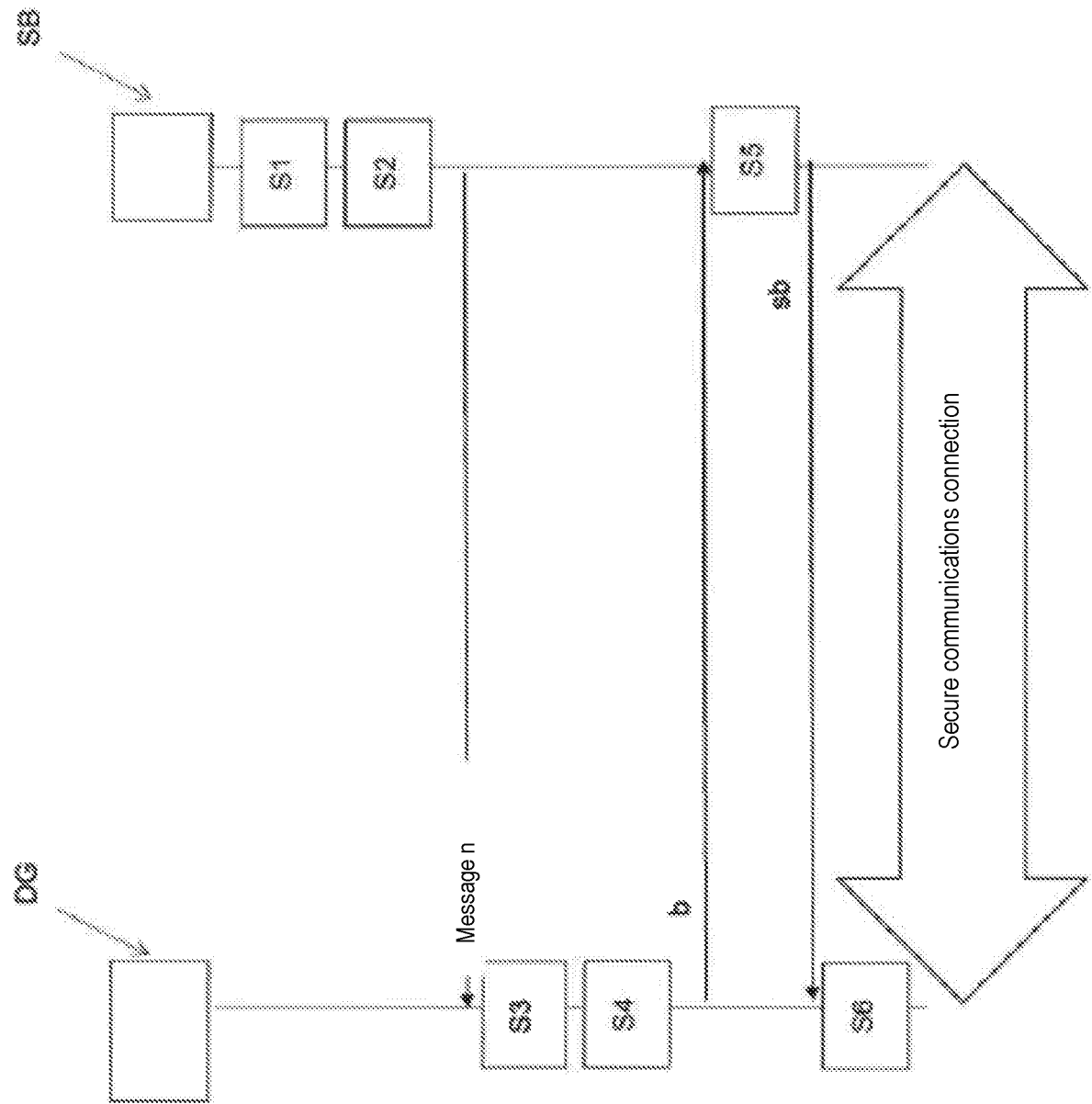
FIG. 5 shows an alternative exemplary interaction diagram with data exchange between the control component and a dialysis machine according to an exemplary variant of the invention.

FIG. 5 illustrates a variant of the process described in FIG. 4 and corresponds in this respect to the structural design described above with reference to FIG. 2. In this case, the protective system is designed as a distributed system and the protective method is performed in a distributed manner. A first stage is performed on the dialysis machine DG and a second stage is performed on the control component SB. As shown in FIG. 5, detecting is performed in step S1 and generating the message n is performed in step S2 on the control component SB. The message n is transmitted to the dialysis machine DG. This preferably also occurs over the secure communications connection. In response thereto, the message n is then output in step S3 and in step S4 the activation of the operating element BE1 is checked. If a confirmation signal b has been detected and the check has thus determined a successful check result, the confirmation signal b can be transmitted in a variant to the control component SB which, in response thereto, sends the control command sb in step S5 to the dialysis machine DG so that it can execute it locally in step S6.

Figure 6:
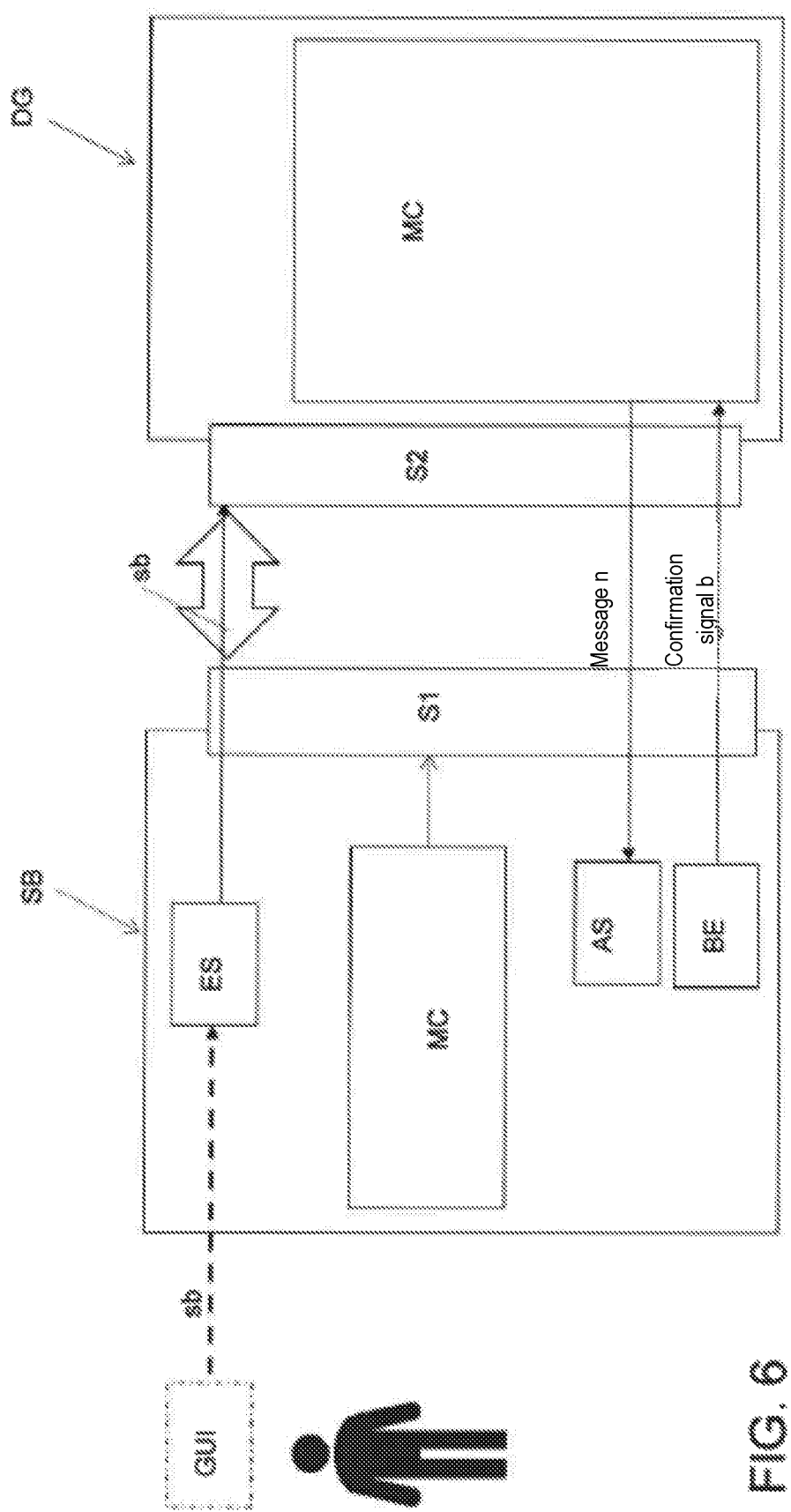
FIG. 6 shows an alternative design relative to the design illustrated in FIG. 1 in which the evaluation logic is formed on the dialysis machine.

FIG. 6 illustrates a variant of the embodiment of the invention shown in FIG. 1 in which the evaluation logic and the safety algorithm are formed at least partly on the dialysis machine DG. The input control command sb is transmitted to the dialysis machine. The processor MC of the dialysis machine DG now implements the detected control command sb in the message (voice or text) and sends this to the output interface AS of the control component SB. Upon activation of the operating element BE on the control component SB, the confirmation signal b is sent back to the dialysis machine DG. Therefore, the previously transmitted control command sb is considered to be confirmed. In other words, the control command sb is only implemented when the confirmation signal b has been received on the dialysis machine DG.

By additionally checking whether or not an operating element has been operated in the preconfigured manner to confirm the detected control command, inputs and control commands on external devices can also be made secure once again by corresponding hardware components. One advantage is that new hardware components do not have to be provided on the terminal (e.g., in the form of new additional operating elements), but rather the already provided operating elements can be used and only have to be actuated in a modified manner by the processor.

It is noted that the description of the invention and the exemplary embodiments are to be understood as being non-limiting with respect to a specific physical implementation of the invention. All features explained and illustrated in conjunction with individual embodiments of the invention can be provided in different combinations in accordance with the invention in order to achieve the advantageous effects thereof at the same time. It is likewise within the scope of the application to require not only the activation of an operating element BE but also the activation of a plurality of operating elements in a predefined sequence (e.g., first loudspeaker volume down and then loudspeaker volume up). Additionally, exemplary embodiments of the invention can be used not just for dialysis machines (e.g., for a hemodialysis machine or a peritoneal dialysis machine) but also for other medical devices which must be controlled in a secure manner via a remote control component SB.

Furthermore, the components of the medical device DG and of the control component SB, such as the user interface GUI, can be implemented in a distributed manner on a plurality of physical products.

It will be appreciated that the execution of the various machine-implemented processes and steps described herein may occur via the execution, by one or more respective processors, of processor-executable instructions stored on a tangible, non-transitory computer-readable medium, such as random access memory (RAM), read-only memory (ROM), programmable read-only memory (PROM), and/or another electronic memory mechanism. Thus, for example, operations performed by a medical device or a computation device as discussed herein may be carried out according to instructions stored on and/or applications installed on one or more respective computing devices.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A control component for detecting control commands for securely controlling a medical device, the control component comprising:
    at least one operating element;
    a user interface configured to:
        detect at least one control command for the medical device; and
        based on detecting the at least one control command, output a message including a request to activate the at least one operating element, wherein the request to activate the at least one operating element comprises a request for simultaneous activation of a plurality of operating elements, wherein the control component is a tablet, smartphone or mobile terminal, and wherein the user interface comprises a graphical user interface (GUI) of the tablet, smartphone or mobile terminal; and
    a processor configured to:
        assign the at least one operating element with an additional function relating to confirming execution of the at least one control command; and
        control the at least one operating element;
    wherein, for confirming execution of the at least one control command, the at least one operating element is configured to detect activation of the at least one operating element; and send a signal to the processor indicating activation of the at least one operating element;
    wherein the processor is further configured to cause execution of the at least one control command on the medical device in response to receiving the signal from the at least one operating element indicating activation of the at least one operating element in accordance with the request;
    wherein the processor is further configured to:
        perform monitoring to determine whether activation of the at least one operating element has already been detected via the at least one operating element before outputting of the message; and in response to determining that activation of the at least one operating element has already been detected via the at least one operating element before outputting of the message, output a warning.

2. The control component according to claim 1, wherein the user interface and the at least one operating element are separate components.

3. The control component according to claim 2, wherein the at least one operating element comprises a switch, a key, a button, or a knob, and wherein the request to activate the at least one operating element comprises a request for performing an action with respect to the switch, the key, the button or the knob.

4. The control component according to claim 1, wherein the control component is arranged separately from the medical device and is configured to communicate with the medical device via a secure communications connection.

5. The control component according to claim 1, wherein the message includes a summary element which reproduces the at least one control command.

6. The control component according to claim 1, wherein the at least one operating element is part of the user interface.

7. A method for operating a control component for detecting control commands for securely controlling a medical device, wherein the control component is arranged separately from the medical device and communicates with the medical device via a secure communications connection, wherein the method comprises:

detecting, by the control component, at least one control command via a user interface of the control component, wherein the control component is a tablet, smartphone or mobile terminal, and wherein the user interface comprises a graphical user interface (GUI) of the tablet, smartphone or mobile terminal;

generating, by the control component, a message including a request to activate at least one operating element, wherein the request to activate the at least one operating element comprises a request for simultaneous activation of a plurality of operating elements;

outputting, by the control component, the message;

checking, by the control component, whether activation of the at least one operating element in accordance with the request has been detected on the at least one operating element; and in response to detecting activation of the at least one operating element in accordance with the request, preparing the at least one control command for execution on the medical device;

wherein the method further comprises:

performing monitoring to determine whether activation of the at least one operating element has already been detected via the at least one operating element before outputting of the message; and in response to determining that activation of the at least one operating element has already been detected via the at least one operating element before outputting of the message, outputting a warning.

8. The method according to claim 7, wherein the at least one control command is detected as an acoustic input.

9. The method according to claim 7, wherein the checking comprises detecting whether a confirmation signal has been received.

10. The method according to claim 7, wherein the at least one control command is detected on an input interface, and wherein the activation of the at least one operating element is not detected on the input interface.

11. The method according to claim 7, wherein the at least one control command and/or the message comprises a time stamp.

12. The method according to claim 7, wherein the request to activate the at least one operating element is generated dynamically in accordance with a preconfigured plan stored in a memory.

13. A non-transitory computer-readable medium having processor-executable instructions stored thereon for operating a control component for detecting control commands for securely controlling a medical device, wherein the control component is arranged separately from the medical device and communicates with the medical device via a secure communications connection, wherein the processor-executable instructions, when executed, facilitate:

detecting, by the control component, at least one control command via a user interface of the control component, wherein the control component is a tablet, smartphone or mobile terminal, and wherein the user interface comprises a graphical user interface (GUI) of the tablet, smartphone or mobile terminal;

generating, by the control component, a message including a request to activate at least one operating element, wherein the request to activate the at least one operating element comprises a request for simultaneous activation of a plurality of operating elements;

outputting, by the control component, the message;

checking, by the control component, whether activation of the at least one operating element in accordance with the request has been detected on the at least one operating element; and in response to detecting activation of the at least one operating element in accordance with the request, preparing the at least one control command for execution on the medical device;

wherein the processor-executable instructions, when executed, further facilitate:

performing monitoring to determine whether activation of the at least one operating element has already been detected via the at least one operating element before outputting of the message; and in response to determining that activation of the at least one operating element has already been detected via the at least one operating element before outputting of the message, outputting a warning.

14. The non-transitory computer-readable medium according to claim 13, wherein the non-transitory computer-readable medium comprises a protected memory region of the control component.

15. A control system for detecting control commands on a control component which is configured for securely controlling a medical device, wherein the control system comprises:

the medical device;

the control component, wherein the control component is a tablet, smartphone or mobile terminal; and at least one operating element;

wherein the control component is arranged separately from the medical device and is configured to communicate with the medical device via a secure communications connection;

wherein the control component or the medical device is configured to detect a control command via a user interface of the control component, wherein the user interface comprises a graphical user interface (GUI) of the tablet, smartphone or mobile terminal;

wherein the control component is configured to generate a message which includes a request to activate the at least one operating element, wherein the request to activate the at least one operating element comprises a request to activate a plurality of operating elements in a defined sequence, and wherein activating the plurality of operating elements in the defined sequence includes first turning a loudspeaker volume up and then turning the loudspeaker volume down;

wherein the control component or the medical device is configured to output the generated message;

wherein, for confirming execution of the at least one control command, the at least one operating element is configured to detect activation of the at least one operating element; and wherein the medical device is configured to execute the at least one control command based on the activation of the at least one operating element being in accordance with the request.

\* \* \* \* \*